United States Patent
Lewis et al.

(10) Patent No.: US 12,036,528 B2
(45) Date of Patent: Jul. 16, 2024

(54) PROCESS FOR REMOVING LEAD IONS FROM BOLDILY FLUIDS USING METALLATE ION EXCHANGE COMPOSITIONS

(71) Applicant: UOP LLC, Des Plaines, IL (US)

(72) Inventors: Gregory J. Lewis, Santa Cruz, CA (US); Paulina Jakubczak, Elk Grove Village, IL (US); James M. Hodges, Evanston, IL (US); Evgeny Kolev, Arlington Heights, IL (US); William Sheets, Glenview, IL (US); Mimoza Sylejmani-Rekaliu, Bensenville, IL (US)

(73) Assignee: UOP LLC, Des Plaines, IL (US)

( * ) Notice: Subject to any disclaimer, the term of this patent is extended or adjusted under 35 U.S.C. 154(b) by 243 days.

(21) Appl. No.: 17/403,335

(22) Filed: Aug. 16, 2021

(65) Prior Publication Data

US 2022/0097019 A1 Mar. 31, 2022

Related U.S. Application Data

(60) Provisional application No. 63/085,784, filed on Sep. 30, 2020.

(51) Int. Cl.
| | | |
|---|---|---|
| *B01J 20/16* | (2006.01) | |
| *A61M 1/36* | (2006.01) | |
| *B01D 15/36* | (2006.01) | |
| *B01J 20/28* | (2006.01) | |

(52) U.S. Cl.
CPC ............ *B01J 20/16* (2013.01); *A61M 1/3679* (2013.01); *B01D 15/362* (2013.01); *B01J 20/28026* (2013.01); *B01D 2257/60* (2013.01)

(58) Field of Classification Search
CPC .. B01J 20/16; B01J 20/28026; A61M 1/3679; B01D 15/362; B01D 2257/60
USPC ......................................................... 502/407
See application file for complete search history.

(56) References Cited

U.S. PATENT DOCUMENTS

| | | | |
|---|---|---|---|
| 4,261,828 A | 4/1981 | Brunner et al. | |
| 4,581,141 A | 4/1986 | Ash | |
| 4,612,122 A | 9/1986 | Ambrus et al. | |
| 5,519,058 A | 5/1996 | Gonick et al. | |
| 5,536,412 A | 7/1996 | Ash | |
| 5,667,695 A | 9/1997 | Bedard et al. | |
| 5,858,243 A | 1/1999 | Bedard | |
| 5,888,472 A | 3/1999 | Bem et al. | |
| 5,891,417 A | 4/1999 | Bem et al. | |
| 6,099,737 A | 8/2000 | Sherman et al. | |
| 6,110,378 A | 8/2000 | Anthony et al. | |
| 6,332,985 B1 | 12/2001 | Sherman et al. | |
| 6,579,460 B1 | 6/2003 | Willis et al. | |
| 6,814,871 B1 | 11/2004 | Bem et al. | |
| 8,802,152 B2 | 8/2014 | Keyser et al. | |
| 8,808,750 B2 | 8/2014 | Keyser et al. | |
| 8,877,255 B2 | 11/2014 | Keyser et al. | |
| 9,033,908 B2 | 5/2015 | Schilthuizen et al. | |
| 9,457,050 B2 | 10/2016 | Keyser et al. | |
| 9,662,352 B2 | 5/2017 | Keyser et al. | |
| 9,707,255 B2 | 7/2017 | Keyser et al. | |
| 9,844,567 B2 | 12/2017 | Keyser et al. | |
| 9,861,658 B2 | 1/2018 | Keyser et al. | |
| 9,913,860 B2 | 3/2018 | Keyser et al. | |
| 9,943,637 B2 | 4/2018 | Keyser et al. | |
| 10,398,730 B2 | 9/2019 | Keyser et al. | |
| 10,413,569 B2 | 9/2019 | Keyser et al. | |
| 2012/0226258 A1 | 9/2012 | Otto et al. | |
| 2017/0165634 A1 | 6/2017 | Shimizu et al. | |
| 2018/0369279 A1 | 12/2018 | Frykman et al. | |

FOREIGN PATENT DOCUMENTS

| | | |
|---|---|---|
| CN | 1239081 A | 12/1999 |
| EP | 0046971 A1 | 3/1982 |
| JP | 2004502508 A | 1/2004 |
| WO | 02096559 A1 | 12/2002 |

OTHER PUBLICATIONS

Guo et al., Bio-inspired detoxification using 3D-printed hydrogel nanocomposites, Nature Communications, May 8, 2014, vol. 5, p. 3774.
Flora et al., Chelation in Metal Intoxication, Int. J. Environ. Res. Public Health, 2010, vol. 7, pp. 2745-2788.
Oleksiienko et al; Titanosilicates in cation adsorption and cation exchange, Chemical Engineering Journal, 2017, vol. 317, pp. 570-585.
Bauer, Rigid Frameworks of Zeolite-Like Compounds of the Pharmacosiderite Structure-Type, Microporous and Mesoporous Materials; 2012, vol. 151, pp. 13-25.

(Continued)

*Primary Examiner* — Edward M Johnson
(74) *Attorney, Agent, or Firm* — Paschall & Associates, LLC; Mark Goldberg

(57) ABSTRACT

A process for removing $Pb^{2+}$ toxins from bodily fluids involves contacting the bodily fluid with an ion exchange composition to remove the metal toxins in the bodily fluid, including blood and gastrointestinal fluid. Alternatively, blood can be contacted with a dialysis solution which is then contacted with the ion exchange composition. The ion exchange compositions are represented by the following empirical formula:

$$A_m Ti_a Nb_{1-a} Si_x O_y$$

having either the pharmacosiderite, sitinakite, pharmacosiderite-sitinakite intergrowth topologies or mixtures thereof. There are also compositions comprising the above ion exchange compositions in combination with bodily fluids or dialysis solution. The ion exchange compositions may be supported by porous networks of biocompatible polymers such as carbohydrates or proteins.

12 Claims, No Drawings

(56) References Cited

OTHER PUBLICATIONS

Tripathi et al., Optimizing Cs-exchange in titanosilicate with the mineral pharmacosiderite topology: framework substitution of Nb and Ge, Journal of Solid State Chemistry, 2004, vol. 177, pp. 2903-2915.
Wani, AB Latif, et al., Lead Toxicity: a Review, Interdiscip Toxicol, 2015, vol. 8(2), 55-64.
International Search Report and Written Opinion for PCT/US2021/071625 date of mailing Dec. 23, 2021.
Office Action for corresponding JP Application No. 2023-519249 dated Mar. 8, 2024.

PROCESS FOR REMOVING LEAD IONS FROM BOLDILY FLUIDS USING METALLATE ION EXCHANGE COMPOSITIONS

This application claims priority from U.S. Provisional Application No. 63/085,784, filed Sep. 30, 2020, which in incorporated herein in its entirety.

FIELD OF THE INVENTION

This invention relates to extracorporeal or intracorporeal processes for removing $Pb^{2+}$ ions from bodily fluids. Gastrointestinal fluid or other bodily fluid is either contacted directly with a metallate ion exchange composition which is capable of selectively removing the toxins or the blood or other bodily fluid is first contacted with a dialysis solution which is then contacted with the metallate ion exchange composition.

BACKGROUND OF THE INVENTION

In mammals, e.g., humans, when the kidneys and/or liver fail to remove metabolic waste products from the body, most of the other organs of the body also soon fail. Accordingly, extensive efforts have been made to discover safe and effective methods for removing toxins from patients' blood by extracorporeal treatment of the blood. Many methods have been proposed for removing small molecular toxins, protein-bound molecules or larger molecules thought to be responsible for the coma and illness of hepatic failure. Some of these toxic compounds have been identified as urea, creatine, ammonia, phenols, mercaptans, short chain fatty acids, aromatic amino acids, false neural transmitters (octopamine), neural inhibitors (glutamate) and bile salts. Among these, phenols and mercaptans, along with bilirubin and bacterial endotoxins, also occur as strong protein-bound toxins and are thus more difficult to effectively remove from the blood. Middle molecular weight toxins having a molecular weight of about 300 to about 10,000 can also be present and are difficult to effectively remove. The art shows a number of ways to treat blood containing such toxins. The classic method is of course dialysis. Dialysis is defined as the removal of substances from a liquid by diffusion across a semipermeable membrane into a second liquid. Dialysis of blood outside of the body (hemodialysis) is the basis of the "artificial kidney." The artificial kidney treatment procedure generally used today is similar to that developed by Kolff in the early 1940s. Since the 1940s there have been several disclosures which deal with improvements on artificial kidneys or artificial livers. Thus, U.S. Pat. No. 4,261,828 discloses an apparatus for the detoxification of blood. The apparatus comprises a housing filled with an adsorbent such as charcoal or a resin and optionally an enzyme carrier. In order to prevent direct contact between the blood and the adsorbent, the adsorbent may be coated with a coating which is permeable for the substances to be adsorbed yet prevent the direct contact between the corpuscular blood components and the adsorbents. U.S. Pat. No. 4,581,141 discloses a composition for use in dialysis which contains a surface adsorptive substance, water, a suspending agent, urease, a calcium-loaded cation exchanger, an aliphatic carboxylic acid resin and a metabolizable organic acid buffer. The calcium loaded cation exchanger can be a calcium-exchanged zeolite. EP 0046971 A1 discloses that zeolite W can be used in hemodialysis to remove ammonia. Finally, U.S. Pat. No. 5,536,412 discloses hemofiltration and plasma filtration devices in which blood flows through the interior of a hollow fiber membrane and during the flow of blood, a sorbent suspension is circulated against the exterior surfaces of the hollow fiber membrane. Another step involves having the plasma fraction of the blood alternately exit and re-enter the interior of the membrane thereby effectuating removal of toxins. The sorbent can be activated charcoal along with an ion-exchanger such as a zeolite or a cation-exchange resin.

There are problems associated with the adsorbents disclosed in the above patents. For example, charcoal does not remove any water, phosphate, sodium or other ions. Zeolites have the disadvantage that they can partially dissolve in the dialysis solution, allowing aluminum and/or silicon to enter the blood. Additionally, zeolites can adsorb sodium, calcium and potassium ions from the blood thereby requiring that these ions be added back into the blood.

More recently, examples of microporous ion exchangers that are essentially insoluble in fluids, such as bodily fluids (especially blood), have been developed, namely the zirconium-based silicates and titanium-based silicates of U.S. Pat. Nos. 5,888,472; 5,891,417 and 6,579,460. The use of these zirconium-based silicate or titanium-based silicate microporous ion exchangers to remove toxic ammonium cations from blood or dialysate is described in U.S. Pat. Nos. 6,814,871, 6,099,737, and 6,332,985. Additionally, it was found that some of these compositions, e.g., UZSi-9, were also selective in potassium ion exchange and could remove potassium ions from bodily fluids to treat the disease hyperkalemia and were also tailored to do so more effectively. Use in treating hyperkalemia is discussed in U.S. Pat. Nos. 8,802,152, 9,457,050, 9,662,352, 9,844,567, 9,861,658, 10,413,569 and 10,398,730 which mention material optimizations such as crystal size, cation form, pH control, ion-exchange capacity, dose format, material combinations such as ZS-9 and ZS-1, a reactor format that yields product devoid of undesirable impurities and simultaneous treatment of hyperammonemia with hyperkalemia. U.S. Pat. Nos. 8,808,750, 8,877,255 and 9,913,860 discuss dosages and combinations of the zirconium silicate materials, including ZS-9 and ZS-7 combinations devoid of ZS-8 for hyperkalemia treatment. U.S. Pat. No. 9,707,255 discusses simultaneous treatment of hyperkalemia and hypercalcemia as well introducing a Ca-exchanged version of ZS-9 that won't absorb too much Ca from the body. Ex-vivo applications of these materials, for instance in dialysis, are described in U.S. Pat. No. 9,943,637.

Blood compatible polymers have also been incorporated into devices for treating bodily fluids. U.S. Pat. No. 9,033,908 discloses small desktop and wearable devices for removing toxins from blood. The device features a sorption filter that utilizes nano-particles embedded in a porous blood compatible polymeric matrix. Among the toxic materials targeted by this device and filter system are potassium, ammonia, phosphate, urea, and uric acid. Similarly, a 3-D printed hydrogel matrix consisting of crosslinked poly(ethylene glycol) diacrylate to which poly diacetylene-based nanoparticles are tethered proved successful for removing the toxin melittin (*Nat. Commun.*, 5, 3774 2014).

Beside toxins derived from metabolic wastes, humans are susceptible to environmental toxins that may enter the body, for instance, by ingestion, absorption through the skin or inhalation. One such toxic metal is lead. For many years, lead was a key component of gasoline in the form of tetraethyl lead and a key component of paints. Currently lead is no longer used or rarely used in these industries, but there are still environmental dangers. Remodeling activities on old homes painted with lead-containing paints produce dusts that may be inhaled or end up in nearby soils and where lead is leached away in ground water or taken up by plants. Unreliable or unregulated water supplies represent a dangerous exposure to $Pb^{2+}$ toxicity, most notably the recent case in Flint, Mich., USA, in which some residents were found to have dangerously high $Pb^{2+}$ levels in their blood after exposure to a new city water supply source. Lead contamination is associated with many ill health effects, including affecting the nervous and urinary systems and inducing learning and developmental disabilities in exposed children. Removal of lead from the blood of afflicted patients would reduce further exposure and damage.

Chelation therapy has also been used for $Pb^{2+}$ poisoning. The chelating agent $CaNa_2EDTA$ has been used to remove $Pb^{2+}$ from blood, but this complex is poorly adsorbed by the gastrointestinal tract and often must be administered intravenously. It was observed that this chelate could mobilize $Pb^{2+}$, transferring it to other tissues, including the brain (*Int. J. Environ. Res. Public Health,* 2010, 7, 2745-2788). Dimercaptosuccinic acid (DMSA) was recognized as an antidote for heavy metal poisoning and has been used to treat $Co^{2+}$, $Cd^{2+}$ and $Pb^{2+}$ poisoning (See U.S. Pat. No. 5,519,058). Concerns about chelation therapy include toxic side effects, non-selective binding of metals, and spread of toxins through the body. Supported chelating agents, i.e., chelating agents bound to resins have been used for heavy metal removal in a dialysis mode, where the blood is on one side of a semi-permeable membrane and the resin-supported chelates on the other side (See U.S. Pat. No. 4,612,122).

Zeolites have been proposed for treating chronic lead poisoning, taken in pill form in US 20180369279A1, but zeolites have limited stability, especially in the gastrointestinal tract.

Recently, applicants disclosed metallate ion exchangers for the removal of $Pb^{2+}$, $Cd^{2+}$, $Cr^{2+}$ and $Co^{2+}$ from bodily fluids in co-pending application Ser. No. 16/506,377. Among the compositions for which $Pb^{2+}$ uptake was demonstrated included titanium-based silicates with the pharmacosiderite and sitinakite topologies. Pharmacosiderite is an iron arsenate mineral and many compositions are known to have the pharmacosiderite topology (See *Micropor. Mesopor. Mater.,* 151, 2012, 13-25). Among the known compositions, Ge and Nb-substituted titanium silicate pharmacosiderite has been disclosed by Tripathi et. al. to optimize $Cs^+$ uptake in ion exchange, see *J. Solid State Chem.,* 177, 2004, 2903-2915. In U.S. Pat. No. 5,667,695, germanium-containing pharmacosiderite ion-exchangers were claimed to uptake many metals, including $Pb^{2+}$, but only demonstrated with $Cs^+$ uptake in pH=13 solution. Similarly, sitinakite is a titanium silicate mineral first reported in *Zap. Vseross Mineral O-va,* 121, 1992, 94-99. A synthetic version of sitinakite, TAM-5, was first discovered by Anthony et al. who noted its favorable $Cs^+$ and $Sr^{2+}$ ion exchange properties (See *Ind Eng. Chem. Res.,* 33, 1994, 2702). A synthesis, crystal structure and ion exchange properties with $Cs^+$ were also reported for sitinakite (See *Chem. Mater.,* 6, 1994, 2364-2368). In U.S. Pat. No. 6,110,378, Anthony et al. reports metal-doped titanium silicate sitinakites, focusing on Nb as the dopant and its superior ability to sequester $Cs^+$ than the undoped material. Further studies on niobium substitution in sitinakite and the resulting $Cs^+$ ion exchange properties were reported in *Micropor. Mesopor. Mater.,* 55, 2002, 1-13. A recent review of the ion-exchange properties of titanium silicate-based materials demonstrate broad utility for this family, but the utility of titanium silicates with the pharmacosiderite and sitinakite topologies has overwhelmingly focused on the removal of $Cs^+$ and $Sr^{2+}$ from nuclear waste stored in high pH solutions (See *Chemical Engineering Journal,* 317, 2017, 570-585).

The pharmacosiderite and sitinakite topologies are alike in two dimensions, differing in the third. Both structures are composed of $[Ti_4O_4]^{8+}$ cubane units, which in the pharmacosiderite topology are linked by $[SiO_4]^{4-}$ tetrahedra in the three primary directions, yielding a cubic three-dimensional 8-ring pore structure. In sitinakite, the bridging $SiO_4$ tetrahedra are present in the a- and b-directions, but not along the c-direction, in which $Ti_4O_4$ groups are linked through a pair of oxide ions, two $O^{2-}$ vs. $SiO_4^{4-}$. This yields a one-dimensional 8-ring pore along the c-direction and 6-ring apertures along the a- and b-directions. The different pore structures are determined by the cations present during the synthesis. When $K^+$ is in the reaction mixture, the pharmacosiderite structure will form. When the cation used in the synthesis is $Na^+$, the sitinakite structure forms. Recognizing the similarities in the pharmacosiderite and sitinakite topologies and the relationships between the chemistry, Bedard disclosed the mixed $K^+$-$Na^+$ synthesis of pharmacosiderite-sitinakite intergrowth structures in U.S. Pat. No. 5,858,243, which is incorporated by reference. The relationship between the pharmacosiderite and sitinakite structures is demonstrated in this disclosure as well as observation of the intergrowth material by transmission electron microscopy. Concurrently with the pharmacosiderite-sitinakite intergrowth is the presence of some pharmacosiderite and sitinakite. Claims of capability were confined to the removal many metals from contaminated liquid streams and did not anticipate utility in the human body. The listed contaminants in the claims of U.S. Pat. No. 5,858,243 include $Pb^{2+}$ but like the pharmacosiderites and sitinakites, the intergrowth was tested for $Cs^+$ uptake in 0.6 M NaOH solution, conditions under which $Pb^{2+}$ would not be soluble or capable of participating in ion exchange processes.

Applicants have developed a process to remove $Pb^{2+}$ toxins from fluids using crystalline metallate ion exchangers that are essentially insoluble in fluids, such as bodily fluids (especially gastrointestinal fluids) or dialysis solutions. These ion exchangers have an empirical formula on an anhydrous basis of:

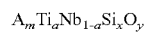

$$A_m Ti_a Nb_{1-a} Si_x O_y$$

where A is an exchangeable cation selected from the group consisting of potassium ion, sodium ion, lithium ion, rubidium ion, cesium ion, calcium ion, magnesium ion, hydronium ion or mixtures thereof, "m" is the mole ratio of A to total metal (total metal=Ti+Nb) and has a value from 0.10 to 2.00, "a" is the mole fraction of total metal that is Ti and has a value from 0.25 to 1, "1-a" is the mole fraction of total metal that is Nb and has a value from zero to 0.75 where a+(1-a)=1, "x" is the mole ratio of Si to total metal and has a value from about 0.25 to 1.50, and "y" is the mole ratio of O to total metal and has a value from 2.55 to about 7.38 and is characterized in that it has the pharmacosiderite topology, sitinakite topology, intergrowths of these two topologies, or mixtures thereof exhibiting an x-ray diffraction pattern having at least one peak with a d-spacing between 7 Å and 8 Å with a relative intensity of 100%, where said diffraction pattern has at least the peaks and d-spacings set forth in Table A when the material has the pharmacosiderite topology:

TABLE A

| 2Θ | d(Å) | I/I₀ % |
|---|---|---|
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m | or where said diffraction pattern has at least the d-spacings and intensities set forth in Table B when the material has the sitinakite topology:

| 2Θ | d(Å) | I/I₀ % |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m | or where said diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination.

Since these compositions are essentially insoluble in bodily fluids (at neutral and acidic or basic pH), they can be orally ingested to remove toxins in the gastrointestinal system as well as used to remove toxins from blood, specifically $Pb^{2+}$.

SUMMARY OF THE INVENTION

As stated, this invention relates to a process for removing $Pb^{2+}$ from fluids selected from the group consisting of a bodily fluid, a dialysate solution and mixtures thereof, the process comprising contacting the fluid containing the toxins with a crystalline metallate ion exchanger resulting in an ion exchanged ion exchanger thereby removing the toxins from the fluid, the metallate ion exchanger selected from titanium silicates and niobium-titanium silicates or mixtures thereof, the metallate having an empirical formula on an anhydrous basis of:

$$A_m Ti_a Nb_{1-a} Si_x O_y$$

where A is an exchangeable cation selected from the group consisting of lithium ion, potassium ion, sodium ion, rubidium ion, cesium ion, calcium ion, magnesium ion, hydronium ion or mixtures thereof, "m" is the mole ratio of A to total metal (total metal=Ti+Nb) and has a value from 0.10 to 2.0, "a" is the mole fraction of total metal that is Ti and has a value from 0.25 to 1, "1-a" is the mole fraction of total metal that is Nb and has a value from zero to 0.75 where a+(1-a)=1, "x" is the mole ratio of Si to total metal and has a value from about 0.25 to 1.50, and "y" is the mole ratio of O to total metal and has a value from 2.55 to about 7.38 and is characterized in that it has either the pharmacosiderite topology, the sitinakite topology, intergrowths of these two topologies, or mixtures thereof exhibiting an x-ray diffraction pattern having at least one peak with a d-spacing between 7 Å and 8 Å with a relative intensity of 100%, where the diffraction pattern has at least the peaks and d-spacings set forth in Table A when the material has the pharmacosiderite topology:

TABLE A

| 2Θ | d(Å) | I/I₀ % |
|---|---|---|
| 11.394-11.163 | 7.76-7.92 | vs |
| 16.281-15.784 | 5.44-5.61 | w |
| 19.959-9.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m | or where said diffraction pattern has at least the d-spacings and intensities set forth in Table B when the material has the sitinakite topology:

| 2Θ | d(Å) | I/I₀ % |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m | or where the diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination. The bodily fluids that are treated by the present invention include blood, gastrointestinal fluids, and dialysis solutions. Blood may include whole blood, blood plasma or other components of blood as known to one of skill in the art.

Another embodiment of the invention is a combination of a bodily fluid or dialysate solution and a crystalline metallate ion exchanger selected from titanium silicates and niobium-titanium silicates or mixtures thereof, the metallate having an empirical formula on an anhydrous basis of:

$$A_m Ti_a Nb_{1-a} Si_x O_y$$

where A is an exchangeable cation selected from the group consisting of lithium ion, potassium ion, sodium ion, rubidium ion, cesium ion, calcium ion, magnesium ion, hydronium ion or mixtures thereof, "m" is the mole ratio of A to total metal (total metal=Ti+Nb) and has a value from 0.10 to 2.0, "a" is the mole fraction of total metal that is Ti and has a value from 0.25 to 1, "1-a" is the mole fraction of total metal that is Nb and has a value from zero to 0.75 where a+(1-a)=1, "x" is the mole ratio of Si to total metal and has a value from about 0.25 to 1.5, and "y" is the mole ratio of O to total metal and has a value from 2.55 to about 7.38 and is characterized in that it has the pharmacosiderite topology, the sitinakite topology, intergrowths of these two topologies, or mixtures thereof exhibiting an x-ray diffraction pattern having at least one peak with a d-spacing between 7 Å and 8 Å with a relative intensity of 100%, where the diffraction pattern has at least the peaks and d-spacings set forth in Table A when the material has the pharmacosiderite topology:

TABLE A

| 2Θ | d(Å) | I/I₀ % |
| --- | --- | --- |
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m | or where the diffraction pattern has at least the d-spacings and intensities set forth in Table B when the material has the sitinakite topology:

| 2Θ | d(Å) | I/I₀ % |
| --- | --- | --- |
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m | or where the diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination.

Another embodiment of the invention is an apparatus incorporating a crystalline metallate ion exchanger selected from titanium silicates and niobium-titanium silicates and mixtures thereof, the composite metallate having an empirical formula on an anhydrous basis of:

$$A_m Ti_a Nb_{1-a} Si_x O_y$$

where A is an exchangeable cation selected from the group consisting of lithium ion, potassium ion, sodium ion, rubidium ion, cesium ion, calcium ion, magnesium ion, hydronium ion or mixtures thereof, "m" is the mole ratio of A to total metal (total metal=Ti+Nb) and has a value from 0.10 to 2.0, "a" is the mole fraction of total metal that is Ti and has a value from 0.25 to 1, "1-a" is the mole fraction of total metal that is Nb and has a value from zero to 0.75 where a+(1-a)=1, "x" is the mole ratio of Si to total metal and has a value from about 0.5 to 1.5, and "y" is the mole ratio of O to total metal and has a value from 2.55 to about 7.38 and is characterized in that it has the pharmacosiderite topology, the sitinakite topology, intergrowths of these two topologies, or mixtures thereof exhibiting an x-ray diffraction pattern having at least one peak with a d-spacing between 7 Å and 8 Å with a relative intensity of 100%, where the diffraction pattern has at least the peaks and d-spacings set forth in Table A when the material has the pharmacosiderite topology:

TABLE A

| 2Θ | d(Å) | I/I₀ % |
| --- | --- | --- |
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m | or where the diffraction pattern has at least the d-spacings and intensities set forth in Table B when the material has the sitinakite topology:

| 2Θ | d(Å) | I/I₀ % |
| --- | --- | --- |
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m | or where said diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination.

The apparatus is configured to contact a bodily fluid or a dialysate solution to remove $Pb^{2+}$ ions. The apparatus of the present invention that contains the above described metallate ion exchanger may be a sorption filter on a wearable device or a device that is remote to the individual. The crystalline metallate ion exchanger may be supported or embedded in a porous biocompatible matrix, including polymers and porous and mesoporous metal oxides and silicates. Natural or biopolymers such as cross-linked carbohydrates or proteins are in particular contemplated as the useful polymers for the present invention.

This and other objects and embodiments will become more clear after a detailed description of the invention.

DETAILED DESCRIPTION OF THE INVENTION

As stated, applicants have developed a new process for removing toxins from fluids selected from bodily fluids and dialysate solution. One essential element of the instant process is an ion exchanger which has a large capacity and strong affinity, i.e., selectivity for $Pb^{2+}$. These compositions are identified as being from titanium silicates and niobium-titanium silicates and mixtures thereof, the composite metallate having an empirical formula on an anhydrous basis of:

$$A_m Ti_a Nb_{1-a} Si_x O_y$$

The composition has a framework structure(s) composed of at least $[TiO_{3/3}O_{3/2}]^-$ octahedral units, $SiO_{4/2}$ tetrahedral units and optionally $NbO_{3/3}O_{3/2}$ octahedral units. "A" is an exchangeable cation selected from the group consisting of potassium ion, lithium ion, sodium ion, rubidium ion, cesium ion, calcium ion, magnesium ion, hydronium ion or mixtures thereof, "m" is the mole ratio of A to total metal (total metal=Ti+Nb) and has a value from 0.10 to 2.0, "a" is the mole fraction of total metal that is Ti and has a value from 0.25 to 1, "1-a" is the mole fraction of total metal that is Nb and has a value from zero to 0.75 where a+(1-a)=1, "x" is the mole ratio of Si to total metal and has a value from about 0.25 to 1.5, and "y" is the mole ratio of O to total metal and has a value from 2.55 to about 7.38 and is characterized in that it has the pharmacosiderite topology, the sitinakite topology, intergrowths of these two topologies, or mixtures thereof exhibiting an x-ray diffraction pattern having at least one peak with a d-spacing between 7 Å and 8 Å with a relative intensity of 100%, where said diffraction pattern has at least the peaks and d-spacings set forth in Table A when the material has the pharmacosiderite topology:

TABLE A

| 2Θ | d(Å) | $I/I_0$ % |
| --- | --- | --- |
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m | or where said diffraction pattern has at least the d-spacings and intensities set forth in Table B when the material has the sitinakite topology:

| 2Θ | d(Å) | $I/I_0$ % |
| --- | --- | --- |
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m | or where the diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination.

The crystalline titanium silicates and niobium-titanium silicates with the pharmacosiderite topology, sitinakite topology, intergrowths of these two topologies, or mixtures thereof are obtained by a hydrothermal crystallization of a reaction mixture prepared by combining a reactive source of titanium, silicon and optionally Nb, at least one alkali metal, a hydroxide source and water. The alkali metal acts as a templating agent. Specific examples of titanium metal sources include, but are not limited to titanium alkoxides, titanium tetrachloride, titanium trichloride and titanium dioxide. The sources of silica include colloidal silica, fumed silica, tetraethylorthosilicate, sodium silicate and potassium silicate. Alkali sources include but are not limited to the nitrate, halide, acetate, carbonate and hydroxide salts including potassium hydroxide, sodium hydroxide, rubidium hydroxide, cesium hydroxide, sodium carbonate, potassium carbonate, rubidium carbonate, cesium carbonate, sodium halide, potassium halide, rubidium halide, cesium halide and lithium acetate. The Nb sources include niobium isopropoxide, niobium ethoxide, hydrous niobium oxide, ammonium niobium oxalate and niobium oxalate. Sources of hydroxide include quaternary ammonium hydroxides ROH, specific examples of which are tetramethylammonium hydroxide, tetraethylammonium hydroxide, tetrapropylammonium hydroxide and tetrabutylammonium hydroxide. Generally, the hydrothermal process used to prepare the crystalline titanium silicates, niobium-titanium silicates and mixtures thereof ion exchange compositions with the pharmacosiderite topology, sitinakite topology, intergrowths of these two topologies, or mixtures thereof of this invention involves forming a reaction mixture which in terms of molar ratios of the oxides is expressed by the formula:

$$r\ R_{2/s}O : p\ A_2O : TiO_2 : a\ Nb_2O_5 : b\ SiO_2 : c\ H_2O$$

where "R" is one or more quaternary ammonium cations, "s" is the charge on the quaternary ammonium cation and is either 1 to 2, "r" has a value of 0 to 25, "p" has a value from about 0.5 to about 25, "a" has a value from about 0 to 1.5, "b" has a value from about 0.25 to 20 and "c" has a value of 10 to 5000. The reaction mixture is prepared by mixing the desired sources of titanium, silicon, optionally Nb, optionally quaternary ammonium hydroxide, and alkali metal in any order to give the desired mixture. It is also necessary that the mixture have a basic pH and preferably a pH of at least 10. The basicity of the mixture is controlled by adding excess alkali hydroxide, quaternary ammonium hydroxide and/or basic compounds of the other constituents of the reaction mixture. Having formed the reaction mixture, it is next reacted at a temperature of about 100° C. to about 200° C. for a period of about 1 to about 30 days in a sealed reaction vessel under autogenous pressure. After the allotted time, the mixture is filtered to isolate the solid product which is washed with deionized water and dried in an oven or simply in air. As stated, the compositions of this invention have a framework with the pharmacosiderite topology, the sitinakite topology, intergrowths of these two topologies, or mixtures thereof, composed of $[TiO_{3/3}O_{3/2}]^-$ octahedral units, $SiO_{4/2}$ tetrahedral units and optionally $NbO_{3/3}O_{3/2}$ octahedral units.

As synthesized, the compositions of this invention will contain some of the alkali metal templating agent in the pores and other charge balancing positions. These metals are described as exchangeable cations, meaning that they can be exchanged with other (secondary) A' cations. Generally, the A exchangeable cations can be exchanged with A' cations selected from other alkali metal cations ($Li^+$, $K^+$, $Na^+$, $Rb^+$, $CO^+$), alkaline earth cations ($Mg^{2+}$, $Ca^{2+}$), hydronium ion (W) or mixtures thereof. It is understood that the A' cation is different from the A cation. The methods used to exchange one cation for another are well known in the art and involve contacting the compositions with a solution containing the desired cation (at molar excess) at exchange conditions. Exchange conditions include a temperature of about 25° C. to about 100° C. and a time of about 20 minutes to about 2 hours. The particular cation (or mixture thereof), which is present in the final product will depend on the particular use of the composition and the specific composition being used. One specific composition is an ion exchanger where the A' cation is a mixture of $Na^+$, $Ca^{2+}$ and $H^+$ ions.

As stated above, the materials of this invention are prepared at high pH and as such may increase the pH of any liquid to which they are exposed. Bodily fluids such as gastrointestinal fluids are acidic throughout the digestive tract, reaching pH values as low as 1.0 in the lower stomach. Blood has a pH of about 7.4. Both of these categories of bodily fluids would experience a rise in pH if exposed directly to the as-synthesized materials of this invention. Therefore, it is preferred to ion exchange the materials of this invention. In one preferred embodiment, the as-synthesized ion-exchanger of the pharmacosiderite topology, sitinakite topology, intergrowths of these two topologies, or mixtures thereof is treated with acid to form the proton/hydronium exchanged version of the ion-exchanger, which avoids the pH rise on contact with bodily fluids. In another embodiment, the as-synthesized ion-exchanger of pharmacosiderite topology, sitinakite topology, intergrowths of these two topologies, or mixtures thereof may be exchanged with $Na^+$ or $Ca^{2+}$ cation or both. In a third embodiment, the as-synthesized ion-exchanger of the pharmacosiderite topology, sitinakite topology, intergrowths of these two topologies, or mixtures thereof may be first ion-exchanged with acid before subsequent ion-exchange with $Na^+$ or $Ca^{2+}$ or both. If the patient being treated for $Pb^{2+}$ poisoning is hypocalcemic, it will be advantageous to use the $Ca^{2+}$ exchanged form of the ion-exchanger of the pharmacosiderite topology, sitinakite topology, intergrowths of these two topologies, or mixtures thereof to avoid reducing $Ca^{2+}$ levels in the patient.

In certain instances, when a quaternary ammonium cation is used in the synthesis, usually as a hydroxide source, the quaternary ammonium cation may be incorporated into the product. Usually, this will not be the case because the quaternary ammonium cations will often be displaced by the alkali cations that have a higher affinity for incorporation into ion exchangers of the pharmacosiderite topology, sitinakite topology, intergrowths of these two topologies, or mixtures thereof. However, any quaternary ammonium ion, if present, must be removed from the product. This can often be accomplished by the ion exchange processes mentioned above. Sometimes the quaternary ammonium ion may be trapped in a pore and it may not be possible to remove the quaternary ammonium cation by ion exchange; a decomposition by calcination will be required. Typically, a calcination consists of heating the sample to a temperature of 400-600° C. for 2-24 hours in flowing air or in flowing nitrogen followed by flowing air. In this process the quaternary ammonium cation is decomposed and replaced by a residual proton. Once the calcination is completed, the sample can be ion exchanged to the desired A' cation composition, as described above.

It is also within the scope of the invention that these ion exchange compositions can be used in powder form or can be formed into various shapes by means well known in the art. Examples of these various shapes include pills, extrudates, spheres, pellets and irregularly shaped particles. This has previously been demonstrated in U.S. Pat. No. 6,579,460 B1 and U.S. Pat. No. 6,814,871 B1. The crystalline ion exchange compositions of this invention may also be supported, ideally in a porous network including insertion into or binding to a blood compatible porous network such as in a sorption filter as disclosed in U.S. Pat. No. 9,033,908 B2. The porous network may consist of natural or synthetic polymers and biopolymers and mesoporous metal oxides and silicates. Natural polymers (biopolymers) that are suitable may comprise a cross-linked carbohydrate or protein, made of oligomeric and polymeric carbohydrates or proteins. The biopolymer is preferably a polysaccharide. Examples of polysaccharides include α-glucans having 1, 3-, 1, 4- and/or 1, 6-linkages. Among these, the "starch family", including amylose, amylopectin and dextrins, is especially preferred, but pullulan, elsinan, reuteran and other α-glucans, are also suitable, although the proportion of 1, 6-linkages is preferably below 70%, more preferably below 60%. Other suitable polysaccharides include ß-1, 4-glucans (cellulose), ß-1, 3-glucans, xyloglucans, glucomannans, galactans and galactomannans (guar and locust bean gum), other gums including heterogeneous gums like xanthan, ghatti, carrageenans, alginates, pectin, ß-2, 1- and ß-2, 6-fructans (inulin and levan), etc. A preferred cellulose is carboxymethylcellulose (CMC, e. g. AKUCELL from AKZO Nobel). Carbohydrates which can thus be used are carbohydrates consisting only of C, H and O atoms such as, for instance, glucose, fructose, sucrose, maltose, arabinose, mannose, galactose, lactose and oligomers and polymers of these sugars, cellulose, dextrins such as maltodextrin, agarose, amylose, amylopectin and gums, e. g., guar. Preferably, oligomeric carbohydrates with a degree of polymerization (DP) from DP2 on or polymeric carbohydrates from DP50 on are used. These can be naturally occurring polymers such as starch (amylose, amylopectin), cellulose and gums or derivates thereof which can be formed by phosphorylation or oxidation. The starch may be a cationic or anionic modified starches. Examples of suitable (modified) starches that can be modified are corn-starch, potato-starch, rice-starch, tapioca starch, banana starch, and manioc starch. Other polymers can also be used (e. g., caprolactone). In certain embodiments, the biopolymer is preferably a cationic starch, most preferably an oxidized starch (for instance C6 oxidized with hypochlorite). The oxidation level may be freely chosen to suit the application of the sorbent material. Very suitably, the oxidation level is between 5 and 55%, most preferably between 25 and 35%, still more preferably between 28% and 32%. Most preferably the oxidized starch is crosslinked. A preferred crosslinking agent is di-epoxide. The crosslinking level may be freely chosen to suit the application of the sorbent material. Very suitably, the crosslinking level is between 0.1 and 25%, more preferably between 1 and 5%, and most preferably between 2.5 and 3.5%. Proteins which can be used include albumin, ovalbumin, casein, myosin, actin, globulin, hemoglobin, myoglobin, gelatin and small peptides. In the case of proteins, proteins obtained from hydrolysates of vegetable or animal material can also be used. Particularly preferred protein polymers are gelatin or a derivative of gelatin.

As stated, these compositions have particular utility in adsorbing various $Pb^{2+}$ metal toxins from fluids selected from bodily fluids, dialysate solutions, and mixtures thereof. As used herein and in the claims, bodily fluids will include but not be limited to blood, blood plasma and gastrointestinal fluids. Also, the compositions are meant to be used to treat bodily fluids of any mammalian body, including but not limited to humans, cows, pigs, sheep, monkeys, gorillas, horses, dogs, etc. The instant process is particularly suited for removing toxins from a human body. There are a number of means for directly or indirectly contacting the fluids with the desired ion exchanger and thus, remove the toxins. One technique is hemoperfusion, which involves packing the above described ion exchange composition into a column through which blood is flowed. One such system is described in U.S. Pat. No. 4,261,828. As stated in the '828 patent, the ion exchange composition is preferably formed into desired shapes such as spheres. Additionally, the ion exchange composition particles can be coated with compounds, such as cellulose derivatives, which are compatible with the blood but nonpermeable for corpuscular blood components. In one specific case, spheres of the desired ion exchange compositions described above can be packed into hollow fibers thereby providing a semipermeable membrane. It should also be pointed out that more than one type of ion-exchange composition can be mixed and used in the process to enhance the efficiency of the process.

Another way of carrying out the process is to prepare a suspension or slurry of the molecular sieve adsorbent by means known in the art such as described is U.S. Pat. No. 5,536,412. The apparatus described in the '412 patent can also be used to carry out the process. The process basically involves passing a fluid, e.g. blood, containing the metal toxins through the interior of a hollow fiber and during said passing, circulating a sorbent suspension against the exterior surfaces of the hollow fiber membrane. At the same time, intermittent pulses of positive pressure are applied to the sorbent solution so that the fluid alternately exits and reenters the interior of the hollow fiber membrane thereby removing toxins from the fluid.

Another type of dialysis is peritoneal dialysis. In peritoneal dialysis, the peritoneal cavity or the abdominal cavity (abdomen) is filled via a catheter inserted into the peritoneal cavity with a dialysate fluid or solution which contacts the peritoneum. Toxins and excess water flow from the blood through the peritoneum, which is a membrane that surrounds the outside of the organs in the abdomen, into the dialysate fluid. The dialysate remains in the body for a time (dwell time) sufficient to remove the toxins. After the required dwell time, the dialysate is removed from the peritoneal cavity through the catheter. There are two types of peritoneal dialysis. In continuous ambulatory peritoneal dialysis (CAPD), dialysis is carried out throughout the day. The process involves maintaining the dialysate solution in the peritoneal cavity and periodically removing the spent dialysate (containing toxins) and refilling the cavity with a fresh dialysate solution. This is carried out several times during the day. The second type is automated peritoneal dialysis or APD. In APD, a dialysate solution is exchanged by a device at night while the patient sleeps. In both types of dialyses, a fresh dialysate solution must be used for each exchange.

The crystalline titanium silicate and titanium-niobium silicate metallate ion exchangers of the present invention can be used to regenerate the dialysate solutions used in peritoneal dialysis, thereby further decreasing the amount of dialysate that is needed to cleanse the blood and/or the amount of time needed to carry out the exchange. This regeneration is carried out by any of the means described above for conventional dialysis. For example, in an indirect contacting process, the dialysate from the peritoneal cavity, i.e. first dialysate which has taken up metal toxins transferred across the peritoneum is now contacted with a membrane and a second dialysate solution and metal toxins are transferred across a membrane, thereby purifying the first dialysate solution, i.e. a purified dialysate solution. The second dialysate solution containing the metal toxins is flowed through at least one adsorption bed containing at least one of the ion exchangers described above, thereby removing the metal toxins and yielding a purified second dialysate solution. It is usually preferred to continuously circulate the second dialysate solution through the adsorbent bed until the toxic metal ions have been removed, i.e., $Pb^{2+}$. It is also preferred that the first dialysate solution be circulated through the peritoneal cavity, thereby increasing the toxic metal removal efficiency and decreasing the total dwell time.

A direct contacting process can also be carried out in which the first dialysate solution is introduced into the peritoneal cavity and then flowed through at least one bed containing at least one ion exchanger. As described above, this can be carried out as CAPD or APD. The composition of the dialysate solution can be varied in order to ensure a proper electrolyte balance in the body. This is well known in the art along with various apparatus for carrying out the dialysis.

The titanium silicate metallates and titanium-niobium silicate metallate ion exchangers can also be formed into pills or other shapes which can be ingested orally and pick up toxins in the gastrointestinal fluid as the ion exchanger passes through the intestines and is finally excreted. To protect the ion exchangers from the high acid content in the stomach, the shaped articles may be coated with various coatings which will not dissolve in the stomach, but dissolve in the intestines.

As has also been stated, although the instant compositions are synthesized with a variety of exchangeable cations ("A"), it is preferred to exchange the cation with secondary cations (A') which are more compatible with blood or do not adversely affect the blood. For this reason, preferred cations are sodium, calcium, hydronium and magnesium. Preferred compositions are those containing sodium and calcium or sodium, calcium and hydronium ions. The relative amount of sodium and calcium can vary considerably and depends on the composition and the concentration of these ions in the blood.

The x-ray patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer-based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$," being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In the x-ray patterns reported, the relative intensities of the d-spacings are indicated by the notations vs, s, m, and w which represent very strong, strong, medium, and weak, respectively. In terms of 100× $I/I_o$, the above designations are defined as:

$$w>0-15; m>15-60:s>60-80 \text{ and } vs>80-100$$

In certain instances, the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the instant invention, the following examples are set forth. It is to be understood that the examples are only by way of illustration and are not intended as an undue limitation on the broad scope of the invention as set forth in the appended claims.

EXAMPLES

Example 1

In a Teflon beaker under a high speed Heidolph stirrer, 306.73 g KOH (87.8%) was dissolved in 576.49 g deionized water and the mixture stirred until reaching room temperature. To this solution, 240.34 g Ludox AS-40 (40% $SiO_2$) was added by the dropperful with vigorous stirring, forming a translucent solution which turned clear after 2 hours of homogenization. To the clear solution, 234.44 g $Ti(OiPr)_4$ (97%) was added via dropperful with continued vigorous overhead stirring. The reaction mixture turned to a white, opaque colloidal-like suspension with an additional stirring. The reaction mixture was loaded into a 2 L Parr stirred reactor and digested 120 hours at 175° C. while stirred at 300 RPM at autogenous pressure. The solid product was isolated by centrifugation, washed with deionized water and dried at 100° C. Powder X-ray diffraction indicated the titanium silicate product had the pharmacosiderite topology; representative diffraction lines are shown below in Table 1. Elemental analysis revealed the stoichiometry of the solid to be $K_{1.40}TiSi_{1.01}$.

TABLE 1

| 2-Θ | d(Å) | I/I$_0$ |
|---|---|---|
| 11.32 | 7.81 | vs |
| 15.95 | 5.55 | w |
| 19.81 | 4.48 | w |
| 22.89 | 3.88 | w |
| 28.00 | 3.18 | m |
| 32.53 | 2.75 | w |
| 34.51 | 2.60 | w |
| 36.53 | 2.46 | w |
| 38.35 | 2.35 | w |
| 40.10 | 2.25 | w |
| 46.52 | 1.95 | w |
| 48.08 | 1.89 | w |
| 49.68 | 1.83 | w |

Example 2

In a Teflon beaker under a high speed Heidolph stirrer, 358.87 g KOH (87.8%) was dissolved in 674.49 g deionized water and the mixture stirred until reaching room temperature. To this solution, 281.20 g Ludox AS-40 (40% SiO$_2$) was added via the dropperful with vigorous overhead stirring forming a clear solution after 2 hours of homogenization. To the clear solution, 274.29 g Ti(OiPr)$_4$ (97%) was added via dropperful with continued overhead stirring. An additional 25 minutes of stirring yielded a white, opaque colloidal-like suspension. The reaction mixture was loaded into a 2 L Parr stirred reactor and digested 120 hours at 175° C. while stirred at 300 RPM at autogenous pressure. The solid product was isolated by centrifugation, washed with deionized water and dried at 100° C. Powder X-ray diffraction revealed the titanium silicate had the pharmacosiderite topology; representative diffraction lines are listed below in Table 2. Elemental analysis indicated the product stoichiometry to be $Na_{0.01}K_{0.97}TiSi_{0.86}$.

TABLE 2

| 2-Θ | d(Å) | I/I$_0$ % |
|---|---|---|
| 11.28 | 7.84 | vs |
| 15.96 | 5.55 | w |
| 19.68 | 4.51 | w |
| 22.83 | 3.89 | w |
| 28.04 | 3.18 | m |
| 32.50 | 2.75 | m |
| 34.52 | 2.60 | w |
| 36.37 | 2.47 | m |
| 38.29 | 2.35 | w |
| 40.10 | 2.25 | w |
| 43.50 | 2.08 | w |
| 46.63 | 1.95 | w |
| 48.10 | 1.89 | w |
| 49.67 | 1.83 | w |

Example 3

In a Teflon beaker under a high speed Heidolph stirrer, 208.11 g KOH (87.3%) was dissolved in 392.42 g deionized water, the resulting solution stirred until reaching room temperature. To this solution, 161.31 g Ludox AS-40 (40% SiO$_2$) was added by the dropperful with vigorous stirring forming a clear solution after 1 hour of homogenization. To the clear solution, 22.71 g hydrous Nb$_2$O$_5$ powder (55.2% Nb) was added and homogenized for 1 hour, creating a smooth white suspension. This was followed by the addition of 115.45 g Ti(OiPr)$_4$ (97%), added by the dropperful with continued overhead stirring. An additional 25 minutes of stirring yielded a white, opaque suspension. The reaction mixture was transferred and sealed in a 2 L Parr stirred reactor and digested 120 hours at 175° C. while stirred at 300 RPM at autogenous pressure. The solid product was isolated by centrifugation, washed with deionized water and dried at 100° C. Powder X-ray diffraction indicated the titanium-niobium silicate had the pharmacosiderite topology. Representative diffraction lines are given in Table 3 below. Elemental analysis indicated the product stoichiometry to be $K_{1.31}Ti_{0.77}Nb_{0.23}Si_{0.91}$.

TABLE 3

| 2-Θ | d(Å) | I/I$_0$ % |
|---|---|---|
| 11.26 | 7.85 | vs |
| 16.14 | 5.49 | w |
| 19.75 | 4.49 | w |
| 22.77 | 3.90 | w |
| 28.01 | 3.18 | s |
| 32.45 | 2.76 | m |
| 34.40 | 2.61 | w |
| 36.52 | 2.46 | w |

Example 4

In a Teflon beaker under a high speed Heidolph stirrer, 45.70 g KOH (87.3%) was dissolved in 87.07 g deionized water, the resulting solution stirred until reaching room temperature. To this solution, 35.42 g Ludox AS-40 (SiO$_2$ 40%) was added by the dropperful with vigorous stirring forming a clear solution after 45 minutes of homogenization. To the clear solution, 2.85 g hydrous Nb$_2$O$_5$ powder (55.2% Nb) was added and allowed to mix for 1 hour, creating a smooth white suspension. Next, 28.97 g Ti(OiPr)$_4$ (97%) was added by the dropperful with continued overhead stirring. With an additional 25 minutes of stirring, the reaction mixture remained a white, opaque suspension. The reaction mixture was loaded into a 300 cc Parr stirred reactor and digested 120 hours at 175° C., stirring at 300 RPM at autogenous pressure. The solid product was isolated by centrifugation, washed with deionized water and dried at 100° C. Powder X-ray diffraction indicated the titanium-niobium silicate had the pharmacosiderite topology. Representative diffraction lines are listed below in Table 4. Elemental analysis indicated the product stoichiometry to be $K_{1.06}Ti_{0.86}Nb_{0.14}Si_{0.89}$.

TABLE 4

| 2-Θ | d(Å) | I/I$_0$ % |
|---|---|---|
| 11.33 | 7.80 | vs |
| 16.03 | 5.53 | w |
| 19.78 | 4.49 | w |

TABLE 4-continued

| 2-Θ | d(Å) | I/I$_0$ % |
|---|---|---|
| 22.81 | 3.90 | w |
| 28.15 | 3.17 | m |
| 32.54 | 2.75 | w |
| 34.55 | 2.59 | w |
| 36.47 | 2.46 | m |
| 46.50 | 1.95 | w |
| 48.01 | 1.89 | w |
| 49.72 | 1.83 | w |

Example 5

A Na$^+$ ion-exchanged version of the as-synthesized material was prepared in the following manner. A 15 g portion of the as-synthesized Ti-silicate pharmacosiderite material from Example 1 was added to 750 ml of 2M NaCl solution, stirred at 75° C. for approximately 1.5 h and filtered to isolate. This process was repeated two more times and the solid washed with deionized water after the last exchange. The solid was dried at 100° C. after the final exchange. Powder X-ray diffraction indicated that the pharmacosiderite topology was retained in the ion-exchanged product. Representative diffraction lines are shown below in Table 5. Elemental analysis showed that most of the K$^+$ in the as-synthesized material had been removed yielding a product stoichiometry of $K_{0.026}Na_{0.80}TiSi_{0.85}$.

TABLE 5

| 2-Θ | d(Å) | I/I$_0$ % |
|---|---|---|
| 11.32 | 7.81 | vs |
| 15.91 | 5.57 | w |
| 19.82 | 4.48 | w |
| 22.76 | 3.90 | w |
| 28.13 | 3.17 | m |
| 32.60 | 2.74 | w |
| 34.38 | 2.61 | w |
| 36.31 | 2.47 | w |
| 38.03 | 2.36 | w |
| 40.18 | 2.24 | w |
| 43.4 | 2.08 | w |
| 46.45 | 1.95 | w |
| 47.94 | 1.90 | w |
| 49.74 | 1.83 | w |

Example 6

A Ca$^{2+}$ ion-exchanged version of the as-synthesized material was prepared in the following manner. An 11.5 g portion of the as-synthesized Ti-silicate pharmacosiderite material from Example 1 was added to 333 ml 1M CaCl$_2$) exchange solution, stirred at 85° C. for 1.5 hr and filtered to isolate. This process was repeated two more and the solid washed with deionized water after the last exchange. The final washed product was dried at 100° C. Powder X-ray diffraction indicated that the pharmacosiderite topology was retained in the Ca$^{2+}$ ion-exchanged product. Representative diffraction lines are shown below in Table 6. Elemental analysis showed that most of the K$^+$ in the as-synthesized material had been removed, yielding a product stoichiometry of $K_{0.13}Ca_{0.47}TiSi_{0.72}$.

TABLE 6

| 2-Θ | d(Å) | I/I$_0$ % |
|---|---|---|
| 11.26 | 7.85 | vs |
| 16.15 | 5.49 | w |
| 19.74 | 4.49 | w |
| 22.77 | 3.90 | w |
| 28.07 | 3.18 | m |
| 32.42 | 2.76 | w |
| 34.46 | 2.60 | w |
| 36.35 | 2.47 | m |
| 38.19 | 2.36 | w |
| 39.94 | 2.26 | w |
| 43.24 | 2.09 | w |
| 46.49 | 1.95 | w |
| 47.96 | 1.90 | m |
| 49.60 | 1.84 | w |

Example 7

An acid-neutralized exchanged form of the Na$^+$-exchanged ion-exchanger was obtained in the following manner. Deionized water, 19.35 g, was treated with 1 M nitric acid to obtain a pH of 1.5. A 2.15 g portion of ground Na$^+$-exchanged Ti-silicate pharmacosiderite material from Example 5 was then suspended in this solution. While monitoring the pH, the suspension was further treated in a dropwise fashion with 1M nitric acid until the pH of the suspension was stable at 1.5 for 20 minutes. This pH stabilization required 9.43 g of the 1M nitric acid. The neutralized material was isolated via filtration, washed with deionized water and dried at 100° C. Powder X-ray diffraction indicated that the pharmacosiderite topology was retained in the acid neutralized product. Representative diffraction lines are shown below in Table 7. Elemental analysis yielded the product stoichiometry of $K_{0.027}Na_{0.0.057}TiSi_{0.81}$, indicating most of cations had been removed, leaving the product predominantly in the hydronium (H$^+$) exchanged form.

TABLE 7

| 2-Θ | d(Å) | I/I$_0$ % |
|---|---|---|
| 11.28 | 7.84 | vs |
| 15.89 | 5.57 | w |
| 19.63 | 4.52 | w |
| 22.57 | 3.94 | w |
| 27.83 | 3.20 | m |
| 32.24 | 2.77 | w |
| 34.34 | 2.61 | w |
| 36.24 | 2.48 | w |
| 38.07 | 2.36 | w |
| 39.76 | 2.27 | w |
| 46.29 | 1.96 | w |
| 47.88 | 1.90 | w |
| 49.16 | 1.85 | w |

Example 8

An acid-neutralized exchanged form of the Ca$^{2+}$-exchanged ion-exchanger was obtained in the following manner. Deionized water, 22.50 g, was treated with 1 M nitric acid to obtain a pH of 1.5. A 2.50 g portion of ground Ca$^{2+}$-exchanged Ti-silicate pharmacosiderite material from Example 6 was then suspended in this solution. While monitoring the pH, the suspension was further treated in a dropwise fashion with 1M nitric acid until the pH of the suspension was stable at 1.5 for 20 minutes. This pH stabilization required 14.97 g of the 1M nitric acid. The neutralized material was isolated via filtration, washed with deionized water and dried at 100° C. Powder X-ray diffraction indicated that the pharmacosiderite topology was retained in the acid neutralized product. Representative diffraction lines are shown below in Table 8. Elemental analysis yielded the product stoichiometry of $K_{0.125}Ca_{0.006}TiSi_{0.92}$, indicating most of cations had been removed, leaving the product predominantly in the hydronium ($H^+$) exchanged form.

TABLE 8

| 2-Θ | d(Å) | I/I₀ % |
|---|---|---|
| 11.28 | 7.84 | vs |
| 16.07 | 5.51 | w |
| 19.62 | 4.52 | w |
| 22.68 | 3.92 | w |
| 27.91 | 3.19 | m |
| 32.33 | 2.77 | w |
| 34.26 | 2.62 | w |
| 36.25 | 2.48 | w |
| 38.07 | 2.36 | w |
| 39.79 | 2.26 | w |
| 46.37 | 1.96 | w |
| 47.90 | 1.90 | w |
| 49.22 | 1.85 | w |

Example 9

The acid exchanged form of the as-synthesized product is obtained in a neutralization procedure implemented as a one stage acid treatment at room temperature, using nitric acid. A 180 g portion of as-synthesized Ti-silicate pharmacosiderite from Example 2 was suspended in 1620 g deionized water with vigorous stirring. The initial pH of the resulting slurry was 12.01. While monitoring the pH, over the course of about an hour, aliquots of 1M $HNO_3$ totaling 26.92 g were added to the stirring slurry until the pH was lowered to and remained consistently in the range of 1.2 to 1.5. The slurry remained in this pH range for 30 minutes post-addition, indicating the pH had stabilized. The product was then isolated via filtration, washed with 10 liters deionized water and dried at 100° C. The effectiveness of this acid treatment to remove the undesirable basicity from the sample is evaluated by examining the pH of a 1:1000 solid:deionized water (by weight) slurry before and after the acid neutralization. The as-synthesized sample of Example 2 yielded a pH of 10.91 in this test, which was reduced to a pH of 4.07 after the acid treatment, a value more compatible with bodily fluids, especially gastrointestinal fluids. Powder X-ray diffraction indicated that the pharmacosiderite topology was retained in the acid treated product, representative diffraction lines are shown below in Table 9. Elemental analysis yielded the product stoichiometry of $K_{0.195}TiSi_{0.82}$, indicating most of cations had been removed, leaving the product predominantly in the hydronium ($H^+$) exchanged form.

TABLE 9

| 2-Θ | d(Å) | I/I₀ % |
|---|---|---|
| 11.26 | 7.85 | vs |
| 15.95 | 5.55 | w |
| 19.58 | 4.53 | w |
| 22.67 | 3.92 | w |
| 27.87 | 3.20 | m |
| 32.28 | 2.77 | w |
| 34.28 | 2.61 | w |
| 36.23 | 2.48 | w |
| 37.99 | 2.37 | w |
| 39.88 | 2.26 | w |
| 46.37 | 1.96 | w |
| 47.70 | 1.91 | w |
| 49.34 | 1.85 | w |
| 52.23 | 1.75 | w |
| 53.65 | 1.71 | w |
| 55.01 | 1.67 | w |
| 57.60 | 1.60 | w |
| 58.87 | 1.57 | w |
| 61.49 | 1.51 | w |

Example 10

While it is desirable to adjust the pH of the ion-exchanger for compatibility as seen in Example 9, it is also desirable to have the appropriate cation form of the ion-exchanger, which often depends on the patient being treated. A $Na^+$ ion-exchanged version of the acid-neutralized material from Example 9 was prepared in the following manner. A 5 g portion of the acid exchanged Ti-silicate pharmacosiderite material from Example 9 was slurried in a solution prepared by dissolving 5 g NaCl in 45 g deionized water, stirred at 80° C. for approximately 1.5 h and filtered to isolate. This process was repeated two more times and the solid washed with deionized water after the last exchange. The solid was dried at 100° C. after the final exchange. Powder X-ray diffraction indicated that the pharmacosiderite topology was retained in the $Na^+$ exchanged, ion-exchanged product. Representative diffraction lines are shown below in Table 10.

TABLE 10

| 2-Θ | d(Å) | I/I₀ % |
|---|---|---|
| 11.26 | 7.85 | vs |
| 15.99 | 5.54 | w |
| 19.62 | 4.52 | w |
| 22.67 | 3.92 | w |
| 27.88 | 3.20 | m |
| 32.28 | 2.77 | w |
| 34.34 | 2.61 | w |
| 36.28 | 2.47 | w |
| 38.09 | 2.36 | w |
| 39.78 | 2.26 | w |
| 46.29 | 1.96 | w |
| 47.86 | 1.90 | w |
| 49.32 | 1.85 | w |
| 52.19 | 1.75 | w |
| 53.61 | 1.71 | w |
| 57.62 | 1.60 | w |
| 58.93 | 1.57 | w |
| 61.47 | 1.51 | w |
| 65.19 | 1.43 | w |
| 67.57 | 1.39 | w |

Example 11

Similar to the $Na^+$-exchanged version of the acid-neutralized ion-exchanger prepared in Example 10, in this example a $Ca^{2+}$ ion-exchanged version of the acid-neutralized material from Example 9 was prepared in the following manner. A 5 g portion of the acid-exchanged Ti-silicate pharmacosiderite material from Example 9 was slurried in a solution prepared by dissolving 5 g $CaCl_2$) in 45 g deionized water, stirred at 80° C. for approximately 1.5 h and filtered to isolate. This process was repeated two more times and the solid washed with deionized water after the last exchange. The solid was dried at 100° C. after the final exchange. Powder X-ray diffraction indicated that the pharmacosiderite topology was retained in the $Na^+$ exchanged, ion-exchanged product. Representative diffraction lines are shown below in Table 11.

TABLE 11

| 2-Θ | d(Å) | I/I₀ % |
|---|---|---|
| 11.22 | 7.88 | vs |
| 16.04 | 5.52 | w |
| 19.63 | 4.52 | w |
| 22.68 | 3.92 | w |
| 27.88 | 3.20 | m |
| 32.30 | 2.77 | w |
| 34.34 | 2.61 | w |
| 36.29 | 2.47 | w |
| 38.09 | 2.36 | w |
| 39.88 | 2.26 | w |
| 46.30 | 1.96 | w |
| 47.88 | 1.90 | w |
| 49.40 | 1.84 | w |
| 52.25 | 1.75 | w |
| 53.65 | 1.71 | w |
| 57.66 | 1.60 | w |
| 58.91 | 1.57 | w |
| 61.51 | 1.51 | w |
| 65.10 | 1.43 | w |
| 67.55 | 1.39 | w |
| 68.73 | 1.36 | w |

Example 12

A solution was prepared by dissolving 3.90 g NaOH (98%) pellets in 111.17 g deionized water using a Heidolph stirrer and stirred until cooled. With continued vigorous stirring, 2.39 g $Nb_2O_5$ powder (55.2% Nb) was added. After 15 minutes of continued vigorous stirring, 9.05 g tetraethylorthosilicate (98%) was added slowly via dropperful. After 15 minutes of continued vigorous overhead stirring, 13.49 g of $Ti(OiPr)_4$ (28.0% as $TiO_2$) was added via dropperful to the reaction mixture immediately forming additional visible precipitate. The white reaction mixture was homogenized for an additional 15 minutes before distribution among 45 ml Teflon-lined Parr reactors, which were digested under a variety of conditions at autogenous pressures. Solid products were isolated by centrifugation, washed 3 times with deionized water and dried in a 100° C. oven overnight. The product isolated after digestion for 18 hours at 200° C. under in a tumbling oven was characterized by X-ray diffraction and identified as sitinakite. Representative x-ray diffraction lines for the product are shown in Table 12. Elemental analysis yielded the stoichiometry $Na_{0.45}Nb_{0.24}Ti_{0.76}Si_{0.55}$.

TABLE 12

| 2-Θ | d(Å) | I/I₀ % |
|---|---|---|
| 11.28 | 7.84 | vs |
| 14.73 | 6.01 | m |
| 17.60 | 5.04 | w |
| 18.61 | 4.76 | w |
| 22.65 | 3.92 | w |
| 26.46 | 3.37 | m |
| 27.44 | 3.25 | m |
| 31.88 | 2.80 | w |
| 32.23 | 2.78 | w |
| 33.94 | 2.64 | m |

TABLE 12-continued

| 2-Θ | d(Å) | I/I₀ % |
|---|---|---|
| 34.26 | 2.62 | m |
| 36.23 | 2.48 | w |
| 36.99 | 2.43 | w |
| 37.49 | 2.40 | w |
| 45.25 | 2.00 | w |
| 45.97 | 1.97 | w |
| 46.23 | 1.96 | w |
| 46.75 | 1.94 | w |
| 47.80 | 1.90 | w |

Example 13

A solution was prepared by dissolving 29.07 g NaOH (98%) pellets in 815.27 g deionized water. With vigorous overhead stirring using a high-speed mechanical stirrer, 49.13 g colloidal silica (Ludox™ AS-40, 40% $SiO_2$) was added slowly but with a single pour. After about an hour of mixing, 106.53 g of $Ti(OiPr)_4$ (97%) was added quickly via a single pour to the translucent colloidal suspension, immediately forming a precipitate. The reaction mixture was homogenized for an additional 5 minutes and loaded into a Parr 2 L autoclave. The mixture was digested for 24 hours at 200° C. quiescently at autogenous pressure. The solid product was isolated by centrifugation, washed 3 times with deionized water and dried in a 100° C. oven overnight. The product was identified as titanium silicate sitinakite by X-ray diffraction. Representative x-ray diffraction lines for the product are shown in Table 13. Elemental analysis provided the stoichiometry $Na_{0.83}TiSi_{0.55}$ for the product.

TABLE 13

| 2-Θ | d(Å) | I/I₀ % |
|---|---|---|
| 11.30 | 7.82 | vs |
| 17.85 | 4.97 | w |
| 22.67 | 3.92 | w |
| 27.25 | 3.27 | m |
| 27.68 | 3.22 | m |
| 32.30 | 2.77 | w |
| 34.50 | 2.60 | m |

Example 14

A Nb—Ti sitinakite/pharmacosidertie intergrowth is prepared according to Example 5 of U.S. Pat. No. 5,935,552. X-ray diffraction indicated the product to be a sitinakite/pharmacosiderite intergrowth. Elemental analysis yielded a stoichiometry of $Na_{0.58}K_{0.26}Ti_{0.81}Nb_{0.19}Si_{0.63}$ for the product.

TABLE 14

| 2-Θ | d(Å) | I/I₀ % |
|---|---|---|
| 11.38 | 7.77 | vs |
| 12.80 | 6.91 | w* |
| 18.02 | 4.92 | w |
| 22.74 | 3.91 | w |
| 26.68 | 3.34 | w |
| 27.14 | 3.28 | m |
| 27.74 | 3.21 | s |
| 28.70 | 3.11 | w* |
| 32.50 | 2.75 | w |
| 34.46 | 2.60 | m |
| 36.36 | 2.47 | w |

TABLE 14-continued

| 2-Θ | d(Å) | I/I$_0$ % |
|---|---|---|
| 37.24 | 2.41 | w |
| 46.48 | 1.95 | w |
| 48.04 | 1.89 | w |

*impurity

Example 15

This is a titanium silicate pharmacosiderite/sitinakite intergrowth preparation adapted from example 5 of U.S. Pat. No. 5,932,552. A solution was prepared dissolving 8.58 g NaOH (98%) pellets and 4.02 g KOH (87%) pellets in 342.4 g deionized water while stirring. Next, 33.0 g Ti(OiPr)$_4$ (97%) was added and stirred for 15 minutes. This was followed by the addition of 27.0 g TEOS (98%) and stirred for 15 minutes. The resulting opaque gel showed was loaded into a 0.6 L stirred Parr reactor. Over a 4 hour period, the temperature of the reaction mixture was ramped to 200° C. and held there for 72 hours with continuous stirring. The solid product was isolated via filtration, washed with deionized water and dried at 90° C. Analysis by powder X-ray diffraction indicated the product to be a sitinakite/pharmacosiderite intergrowth. Representative diffraction lines for the product are shown in Table 15. Elemental analysis yielded the stoichiometry Na$_{0.64}$K$_{0.27}$TiSi$_{0.81}$ for the product.

TABLE 15

| 2-Θ | d(Å) | I/I$_0$ % |
|---|---|---|
| 11.44 | 7.73 | vs |
| 16.37 | 5.41 | w |
| 19.56 | 4.53 | w |
| 23.04 | 3.86 | w |
| 28.02 | 3.18 | m |
| 32.70 | 2.74 | w |
| 34.49 | 2.60 | w |
| 36.57 | 2.45 | w |
| 46.58 | 1.95 | w |
| 48.23 | 1.89 | w |
| 49.70 | 1.83 | w |
| 58.94 | 1.57 | w |

Example 16: Removal of Pb$^{2+}$ Ions from Solution

The samples disclosed in Examples 1-15 were tested to determine their ability to selectively adsorb Pb$^{2+}$ ions from a solution that also contained essential electrolytes found in the body, including Na, K, Mg, and Ca. The test solutions were prepared by dissolving sodium nitrate, potassium nitrate, magnesium nitrate, calcium nitrate, and lead nitrate in a sodium acetate buffer solution. Sodium acetate buffer solution, 1 L, was prepared by dissolving 4.18 g sodium acetate and 2.49 g acetic acid in 1 L of deionized water. The buffer solution was used to maintain a constant pH of approximately 4.7 during testing. The test solutions were first analyzed by ICP and contained approximate concentrations of 3000 ppm Na$^+$, 300 ppm K$^+$, 25 ppm Mg$^{2+}$, 25 ppm Ca$^{2+}$ and either 200 ppb Pb$^{2+}$ or 15 ppm Pb$^{2+}$. For the test, 100 mg of the titanium silicate or titanium-niobium silicate pharmacosiderite ion exchanger was placed in a 125 mL plastic bottle along with 100 mL of the testing solution. The capped bottles were tumbled at room temperature for 2 hours. Once the ion-exchanger has been in contact with the test solution for the desired amount of time, the solid/solution suspension is passed through a 0.2 µm syringe filter to remove the solids, and then the solution is analyzed using ICP. The K$_d$ value for the distribution of metals between solution and solid was calculated using the following formula:

$$K_d(mL/g) = \frac{(V)(Ac)}{(W)(Sc)} 1$$

where:
V=volume of waste simulant (mL)
Ac=concentration of cation absorbed on ion-exchanger (g/mL)
W=mass of ion-exchanger evaluated (g)
Sc=concentration of cation in post reaction supernatant (g/mL)

Table 16 below summarizes the results of the Pb$^{2+}$ uptake studies, initial and final Pb$^{2+}$ concentrations and the K$_d$ values are given. The disclosed ion-exchangers in this application remove at least 50% of the Pb$^{2+}$ from the test solution. The ion-exchangers did not remove significant amounts of the complimentary essential electrolytes Na$^+$, Mg$^{2+}$ or Ca$^{2+}$.

TABLE 16

| Example | Pb$_i$ (ppb) | Pb$_f$ (ppb) | K$_d$ | Pb$_i$ (ppm) | Pb$_f$ (ppm) | K$_d$ |
|---|---|---|---|---|---|---|
| 1 | 213 | 47.4 | 3494 | | | |
| 2 | 200 | 63.1 | 2170 | 14.70 | 6.61 | 1224 |
| 3 | 200 | 39.4 | 4076 | 14.70 | 6.29 | 1337 |
| 4 | | | | 14.70 | 2.38 | 5176 |
| 5 | 224 | 5.6 | 39000 | | | |
| 6 | 224 | 9.2 | 23348 | | | |
| 7 | 193 | 31.3 | 5166 | | | |
| 8 | 193 | 32.5 | 4938 | | | |
| 9 | 200 | 56.2 | 2559 | 14.70 | 4.19 | 2508 |
| 10 | | | | 14.70 | 3.16 | 3652 |
| 11 | | | | 14.70 | 3.44 | 3273 |
| 12 | | | | 15.40 | 0.551 | 26949 |
| 13 | | | | 15.40 | 0.181 | 84083 |
| 14 | | | | 14.70 | 1.70 | 7647 |
| 15 | | | | 14.70 | 3.49 | 3212 |

Specific Embodiments

While the following is described in conjunction with specific embodiments, it will be understood that this description is intended to illustrate and not limit the scope of the preceding description and the appended claims.

A first embodiment of the invention is a process for removing Pb$^{2+}$ toxins from bodily fluids comprising contacting the fluid containing the toxins with an ion exchanger to remove the toxins from the fluid by ion exchange between the ion exchanger and the bodily fluid, the crystalline metallate ion exchanger selected from titanium silicates and niobium-titanium silicates or mixtures thereof, the metallate having an empirical formula on an anhydrous basis of:

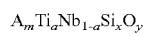

$$A_mTi_aNb_{1-a}Si_xO_y$$

where A is an exchangeable cation selected from the group consisting of lithium ion, potassium ion, sodium ion, rubidium ion, cesium ion, calcium ion, magnesium ion, hydronium ion or mixtures thereof, "m" is the mole ratio of A to total metal (total metal=Ti+Nb) and has a value from 0.10 to 2.0, "a" is the mole fraction of total metal that is Ti and has a value from 0.25 to 1, "1-a" is the mole fraction of total metal that is Nb and has a value from zero to 0.75 where a+(1-a)=1, "x" is the mole ratio of Si to total metal and has a value from about 0.25 to 1.50, and "y" is the mole ratio of O to total metal and has a value from 2.5 to about 7.38 and is characterized in that it has the either the pharmacosiderite topology, sitinakite topology, intergrowths of these two topologies, or mixtures thereof exhibiting an x-ray diffraction pattern having at least one peak with a d-spacing between 7 Å and 8 Å with a relative intensity of 100%, where said diffraction pattern has at least the peaks and d-spacings set forth in Table A when the material has the pharmacosiderite topology:

TABLE A

| 2Θ | d(Å) | I/I$_0$ % |
|---|---|---|
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m | or where said diffraction pattern has at least the d-spacings and intensities set forth in Table B when the material has the sitinakite topology:

TABLE B

| 2Θ | d(Å) | I/I$_0$ % |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m | or where said diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination.

Specific Embodiments

An embodiment of the invention is one, any or all of prior embodiments in this paragraph up through the first embodiment in this paragraph wherein the bodily fluid is selected from the group consisting of whole blood, blood plasma, or other component of blood, gastrointestinal fluids, dialysate fluids, gastrointestinal fluids and dialysate solution containing blood, blood plasma, other component of blood or gastrointestinal fluids. An embodiment of the invention is one, any or all of prior embodiments in this paragraph up through the first embodiment in this paragraph where a=1. An embodiment of the invention is one, any or all of prior embodiments in this paragraph up through the first embodiment in this paragraph where a=0.5. An embodiment of the invention is one, any or all of prior embodiments in this paragraph up through the first embodiment in this paragraph where A is hydronium (H$^+$). An embodiment of the invention is one, any or all of prior embodiments in this paragraph up through the first embodiment in this paragraph where A is sodium. An embodiment of the invention is one, any or all of prior embodiments in this paragraph up through the first embodiment in this paragraph where A is calcium. An embodiment of the invention is one, any or all of prior embodiments in this paragraph up through the first embodiment in this paragraph where A is a mixture of calcium and sodium. An embodiment of the invention is one, any or all of prior embodiments in this paragraph up through the first embodiment in this paragraph where A is a mixture of calcium, sodium and hydronium (H$^+$). An embodiment of the invention is one, any or all of prior embodiments in this paragraph up through the first embodiment in this paragraph wherein the ion exchanger is packed into hollow fibers incorporated into a membrane. An embodiment of the invention is one, any or all of prior embodiments in this paragraph up through the first embodiment in this paragraph wherein the ion exchanger is contained on particles coated with a coating comprising a cellulose derivative composition. An embodiment of the invention is one, any or all of prior embodiments in this paragraph up through the first embodiment in this paragraph wherein the process is a hemoperfusion process wherein the bodily fluid is passed through a column containing the ion exchanger. An embodiment of the invention is one, any or all of prior embodiments in this paragraph up through the first embodiment in this paragraph wherein a dialysate solution is introduced into a peritoneal cavity and then is flowed through at least one adsorbent bed containing at least one of the ion exchanger. An embodiment of the invention is one, any or all of prior embodiments in this paragraph up through the first embodiment in this paragraph wherein the ion exchanger is formed into a shaped article to be ingested orally, followed by ion exchange between the ion exchanger and the Pb$^{2+}$ toxins contained in a gastrointestinal fluid in a mammal's intestines and then by excretion of the ion exchanger containing the toxins. An embodiment of the invention is one, any or all of prior embodiments in this paragraph up through the first embodiment in this paragraph wherein the shaped article is coated with a coating that is not dissolved by conditions within a stomach.

A second embodiment of the invention is a composition comprising a combination of a bodily fluid, a dialysate solution or a mixture of the bodily fluid and the dialysate solution the combination further comprising an ion exchanger, the crystalline metallate ion exchanger selected from titanium silicates and niobium-titanium silicates or mixtures thereof, the metallate having an empirical formula on an anhydrous basis of:

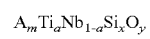

$$A_m Ti_a Nb_{1-a} Si_x O_y$$

where A is an exchangeable cation selected from the group consisting of lithium ion, potassium ion, sodium ion, rubidium ion, cesium ion, calcium ion, magnesium ion, hydronium ion or mixtures thereof, "m" is the mole ratio of A to total metal (total metal=Ti+Nb) and has a value from 0.10 to 2.0, "a" is the mole fraction of total metal that is Ti and has a value from 0.25 to 1, "1-a" is the mole fraction of total metal that is Nb and has a value from zero to 0.75 where a+(1-a)=1, "x" is the mole ratio of Si to total metal and has a value from about 0.25 to 1.50, and "y" is the mole ratio of O to total metal and has a value from 2.55 to about 7.38 and is characterized in that it has the either the pharmacosiderite topology, sitinakite topology, intergrowths of these two topologies, or mixtures thereof exhibiting an x-ray diffraction pattern having at least one peak with a d-spacing between 7 Å and 8 Å with a relative intensity of 100%, where said diffraction pattern has at least the peaks and d-spacings set forth in Table A when the material has the pharmacosiderite topology:

TABLE A

| 2Θ | d(Å) | I/I₀ % |
|---|---|---|
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m | or where said diffraction pattern has at least the d-spacings and intensities set forth in Table B when the material has the sitinakite topology:

TABLE B

| 2Θ | d(Å) | I/I₀ % |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m | or where said diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination. An embodiment of the invention is one, any or all of prior embodiments in this paragraph up through the second embodiment in this paragraph wherein the bodily fluid is whole blood, blood plasma, other blood component or gastrointestinal fluid.

A third embodiment of the invention is an apparatus comprising a matrix containing a support material for an ion exchanger, the crystalline metallate ion exchanger selected from titanium silicates and niobium-titanium silicates or mixtures thereof, the metallate having an empirical formula on an anhydrous basis of:

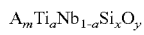

$$A_m Ti_a Nb_{1-a} Si_x O_y$$

where A is an exchangeable cation selected from the group consisting of lithium ion, potassium ion, sodium ion, rubidium ion, cesium ion, calcium ion, magnesium ion, hydronium ion or mixtures thereof, "m" is the mole ratio of A to total metal (total metal=Ti+Nb) and has a value from 0.10 to 2.0, "a" is the mole fraction of total metal that is Ti and has a value from 0.25 to 1, "1-a" is the mole fraction of total metal that is Nb and has a value from zero to 0.75 where a+(1-a)=1, "x" is the mole ratio of Si to total metal and has a value from about 0.25 to 1.50, and "y" is the mole ratio of O to total metal and has a value from 2.55 to about 7.38 and is characterized in that it has the either the pharmacosiderite topology, sitinakite topology, intergrowths of these two topologies, or mixtures thereof exhibiting an x-ray diffraction pattern having at least one peak with a d-spacing between 7 Å and 8 Å with a relative intensity of 100%, where said diffraction pattern has at least the peaks and d-spacings set forth in Table A when the material has the pharmacosiderite topology:

TABLE A

| 2Θ | d(Å) | I/I₀ % |
|---|---|---|
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m | or where said diffraction pattern has at least the d-spacings and intensities set forth in Table B when the material has the sitinakite topology:

TABLE B

| 2Θ | d(Å) | I/I₀ % |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m | or where said diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination.

An embodiment of the invention is one, any or all of prior embodiments in this paragraph up through the third embodiment in this paragraph wherein the matrix comprises a porous network comprising biocompatible polymers and metal oxides and silicates. An embodiment of the invention is one, any or all of prior embodiments in this paragraph up through the third embodiment in this paragraph wherein the biocompatible polymers comprise cross-linked carbohydrates or proteins. An embodiment of the invention is one, any or all of prior embodiments in this paragraph up through the third embodiment in this paragraph wherein the biocompatible polymer is a polysaccharide selected from α-glucans having 1, 3-, 1, 4- or 1, 6 linkages. An embodiment of the invention is one, any or all of prior embodiments in this paragraph up through the third embodiment in this paragraph wherein the biocompatible polymer is a carbohydrate selected from glucose, fructose, sucrose, maltose, arabinose, mannose, galactose, lactose and oligomers and polymers comprising one or more of the carbohydrates. An embodiment of the invention is one, any or all of prior embodiments in this paragraph up through the third embodiment in this paragraph wherein the biocompatible polymer comprises a protein selected from albumin, ovalbumin, casein, myosin, actin, globulin, hemoglobin, myoglobin, gelatin and small peptides.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

We claim as our invention:

1. A process for removing $Pb^{2+}$ toxins or mixtures thereof from bodily fluids comprising contacting the bodily fluid containing the toxins with a crystalline metallate ion exchanger to remove the toxins from the fluid by ion exchange between said crystalline metallate ion exchanger and said bodily fluid, the crystalline metallate ion exchanger selected from titanium silicates and niobium-titanium silicates or mixtures thereof, the metallate having an empirical formula on an anhydrous basis of:

$$A_m Ti_a Nb_{1-a} Si_x O_y$$

where A is an exchangeable cation selected from the group consisting of lithium ion, potassium ion, sodium ion, rubidium ion, cesium ion, calcium ion, magnesium ion, hydronium ion and mixtures thereof, "m" is the mole ratio of A to total metal (total metal=Ti+Nb) and has a value from 0.10 to 2.0, "a" is the mole fraction of total metal that is Ti and has a value from 0.25 to 1, "1-a" is the mole fraction of total metal that is Nb and has a value from zero to 0.75 where a+(1-a)=1, "x" is the mole ratio of Si to total metal and has a value from about 0.25 to 1.50, and "y" is the mole ratio of O to total metal and has a value from 2.55 to about 7.38 and is characterized by having a pharmacosiderite topology, a sitinakite topology, intergrowths of said pharmacosiderite topology and said sitinakite topology, or mixtures thereof and exhibiting an x-ray diffraction pattern having at least one peak with a d-spacing between 7 Å and 8 Å with a relative intensity of 100%, where said diffraction pattern has peaks and d-spacings set forth in Table A when the crystalline metallate ion exchanger has the pharmacosiderite topology:

TABLE A

| 2Θ | d(Å) | I/I₀ % |
|---|---|---|
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m | or where said diffraction pattern has at least the d-spacings and intensities set forth in Table B when the crystalline metallate ion exchanger has the sitinakite topology:

TABLE B

| 2Θ | d(Å) | I/I₀ % |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m | or where said diffraction pattern has at least one peak with a d-spacing between 7 Å and 8 Å with a relative intensity of 100% when the crystalline metallate ion exchanger is a pharmacosiderite-sitinakite intergrowth or a mixture of pharmacosiderite, sitinakite and pharmacosiderite-sitinakite intergrowth phases in any combination.

2. The process of claim 1 wherein the bodily fluid is selected from the group consisting of whole blood, blood plasma, or other component of blood, gastrointestinal fluids, dialysate fluids, gastrointestinal fluids and dialysate solution containing blood, blood plasma, other component of blood and gastrointestinal fluids.

3. The process of claim 1 where the ion-exchanger has the phamacosiderite topology.

4. The process of claim 1 where the ion-exchanger has the sitinakite topology.

5. The process of claim 1 where the ion-exchanger is an intergrowth of the phamacosiderite and sitinakite topologies.

6. The process of claim 1 where the ion-exchanger is a composite comprised of a mixture of the phamacosiderite, sitinakite, pharmacosiderite-sitinakite intergrowth topologies in any combination.

7. The process of claim 1 where a=1.

8. The process of claim 1 where A is hydronium ($H^+$).

9. The process of claim 1 where A is calcium.

10. The process of claim 1 where A is sodium.

11. The process of claim 1 where A is a mixture of hydronium ($H^+$), calcium and sodium.

12. The process of claim 1 wherein said ion exchanger is formed into a shaped article to be ingested orally, followed by ion exchange between said ion exchanger and said $Pb^{2+}$ toxins contained in a gastrointestinal fluid in a mammal's intestines and then by excretion of said ion exchanger containing said toxins.

* * * * *